United States Patent [19]

Cantrell

[11] Patent Number: 4,503,048

[45] Date of Patent: Mar. 5, 1985

[54] PYRIDINE SOLUBLE EXTRACT OF A MICROORGANISM

[75] Inventor: John L. Cantrell, Hamilton, Mont.

[73] Assignee: Ribi ImmunoChem Research, Inc., Hamilton, Mont.

[21] Appl. No.: 632,256

[22] Filed: Jul. 18, 1984

Related U.S. Application Data

[63] Continuation of Ser. No. 393,821, Jun. 30, 1982, abandoned.

[51] Int. Cl.³ .............................................. A61K 35/78
[52] U.S. Cl. ..................................................... 424/195
[58] Field of Search ......................................... 424/195

[56] References Cited

U.S. PATENT DOCUMENTS 3,956,481  5/1976  Jolles et al. ............................ 424/92
3,976,544  8/1976  Adam et al. ........................... 424/92

OTHER PUBLICATIONS

Meyer et al., J. Natl. Can. Inst. 52:103–108, 1974.
Ribi et al., Natl. Can. Inst. Monograph, No. 39, 1974.
Rozencweig et al., Can. 40:334–342, 1977.
Pharmacological Basis of Can. Chem., William & Wilkins Co., 1975, pp. 249–270.

Primary Examiner—Jerome D. Goldberg
Assistant Examiner—John W. Rollins
Attorney, Agent, or Firm—Burgess, Ryan & Wayne

[57] ABSTRACT

A method of producing a purified pyridine-soluble extract of a microorganism is disclosed which contains between about 7 and 20% by weight of protein, between about 10 and 16% by weight of sugar, and between about 35 and 55% by weight of fatty acids. The extract when combined with cell wall skeleton in a pharmaceutically acceptable medium is useful as an anti-tumor agent in the treatment of animals.

9 Claims, No Drawings

PYRIDINE SOLUBLE EXTRACT OF A MICROORGANISM

This application is a continuation of application Ser. No. 393,821, filed June 30, 1982 now abandoned.

BACKGROUND OF THE INVENTION

The present invention is directed to a pyridine-soluble extract of a microorganism which, when combined with cell wall skeleton (CWS), provides a pharmaceutical composition possessing anti-animal tumor properties.

Bacteria such as *Corynebacterium parvum* have been the subject of experimental work to isolate and characterize the component responsible for inducing inhibition of tumor growth [see, for example, *Anti Tumor Activity and Lymphoreticular Stimulation Properties of Fractions Isolated from C. parvum;* Cantrell, et al, Cancer Research 39, pgs. 3554–3563 (September, 1979)]. Apart from anti-tumor activity, *C. parvum* has shown to be a potent stimulator of the lymphoreticular system resulting in undesirable increases in spleen and liver weights and blastogenesis. Applicant has discovered that a pyridine-soluble extract of microorganism possesses potent anti-animal tumor properties without the undesirable toxic effects associated with the prior art products.

Cell wall skeleton is essentially cell wall which has had much of the protein and lipids normally found in the cell wall removed. It is a polymeric mycolic acid arabinogalactan mucopeptide containing remnants of trehalose mycolates ("P3") and undigested tuberculoproteins. Cell wall skeleton is obtained from any microorganism including, but not limited to, *M.smegmatis, M.phlei, Nocardia rubra, Nocardia asteroides, Corynebacterium diphtheria, Corynebacterium parvum, M.kansasii, M.tuberculosis* (Strain H 37 RV and Ayoma B), and *M.bovis* Strain BCG. Additionally, cell wall skeleton may be obtained from such other microorganisms as *E.coli, B.abortus* and *Coxiella burnettii*.

Cell wall skeleton may be produced by first growing and harvesting bacteria such as *M.bovis* Strain BCG (Bacillus Calmette - Guerin). The resulting whole cell residue is processed through a cell fractionator [Ribi Cell Fractionator (Sorvall, Model RF-1)] which disrupts the cells, separating the outer envelope or cell wall from the protoplasmic impurities. The resulting cell walls are then subjected to a series of solvent extractions and enzymatic treatments (e.g., trypsin and/or chymotrypsin) to give purified cell wall skeleton.

It is, therefore, an object of the present invention to provide a pharmaceutical composition containing a pyridine-soluble extract of a microorganism in combination with cell wall skeleton.

It is another object of the invention to provide a method of producing the pyridine-soluble extract of a microorganism.

It is still another object of the invention to provide a method of treating tumors in warm blooded animals using the composition containing the pyridine-soluble extract of a microorganism and cell wall skeleton.

SUMMARY OF THE INVENTION

The present invention relates to pharmaceutical compositions comprising a pyridine-soluble extract of a microorganism, containing between about 7 and 20% by weight of protein and about 10 to 16% by weight of sugar, and about 35 to 55% by weight of fatty acids in combination with cell wall skeleton (CWS). The extract preferably contains about 12% by weight of each of protein and sugar and about 45% by weight of fatty acids.

Any microorganism may be used to obtain the pyridine-soluble extract including, for example, *M. bovis* BCG, *M. phlei, M. smegmatis, M. kansasii, Nocardia rubra, Corynebacterium diphtheriae* and *Corynebacterium parvum*. *Corynebacterium parvum* is especially preferred.

Whole cells of the microorganism, preferably in the form of a paste, are mixed with pyridine. The resulting mixture is separated to obtain a supernatant fraction which contains the pyridine-soluble extract and a pyridine residue. Optionally, the pyridine residue may be subjected to repeated separation procedures as described above using pyridine to remove further quantities of the desired extract.

The pyridine is then removed from the extract and the dried extract is dialyzed against a suitable liquid such as distilled water. The absence of whole cells or cell fragment contaminants is confirmed by electron microscopy. The resulting purified extract may then be lyophilized by known methods to obtain a stable product.

The pyridine-soluble extract produced in accordance with this invention may be combined with CWS to produce a composition having potent anti-animal tumor activity without stimulating the induction of spleen and liver enlargements. The cancers which may be treated by this composition include animal tumors such as bovine squamous cell carcinoma, bovine fibrosarcoma, equine sarcoid, equine melanoma, equine squamous cell carcinoma, canine mammary tumors, canine adenoma and canine melanoma.

The composition is preferably administered by injection in a pharmaceutically acceptable medium such as an oil-droplet emulsion directly into the tumor under conditions more particularly described below. The aforesaid composition may be stabilized as for example, by a lyophilization procedure and then reconstituted without loss of potency.

The amount of the pyridine-soluble extract in a single injection for the treatment of animals is between about 375 and 2500 micrograms/milliliter. The amount of CWS is between about 125 and 375 micrograms/milliliter.

The number of milliliters of the biologic injected into the tumor is determined by the size of the tumor in accordance with the following table:

| Animal Dosage According to Tumor Size | |
| --- | --- |
| Diameter of Tumor (cm) | Amount of Biologic Injected (ml) |
| 0–1 | up to 0.5 |
| 1–2 | 0.5 to 2.5 |
| 2–3 | 2.5 to 5 |
| 3–5 | 5 to 10 |
| 5–8 | 10 to 15 |
| greater than 8 | 15 to 20 |

The maximum dose per injection is about 40 milligrams for each of the pyridine-soluble extract and CWS. The course of treatment comprises up to six injections administered at about two week intervals.

The present composition is a suitable injection medium such as an oil-droplet emulsion is administered directly into tumors. The amount of the pyridine-soluble extract in a single injection is between about 200 and 5000 micrograms, preferably between about 800 and 1200 micrograms, while the amount of CWS is between about 50 and 2000 micrograms. The preferred single dosage level for CWS is between about 475 and 525 micrograms. All of the above-mentioned dosage levels are based on a typical 70 kilogram adult animal. The injections are administered about once every week for up to a total of 15 injections.

As described above, the composition for treatment of warm blooded animals may be used in the form of an oil droplet emulsion. The amount of oil used is in the range of between about 0.5 and 3.0 percent by volume based on the total volume of the composition. It is preferred to use between about 0.75 and 1.5 percent by volume of the oil. Examples of such oils include light mineral oil, squalane, squalene, and 7-n-hexyloctadecane.

The homogenized oil containing mixture is then combined with a detergent which may optionally be dissolved in a saline solution prior to mixing. The amount of detergent is typically between about 0.02 and 0.25 percent by volume and preferably between about 0.10 and 0.20 percent by volume based on the total volume of the composition. Any common detergent material may be used including Tween-80 and Arlacel (produced by the Atlas Chemical Company).

The mixture resulting from the addition of detergent is then homogenized to form a suspension which has a high percentage of oil droplets coated with the active components as determined by observation under a microscope.

The following examples are for illustrative purposes only and are not intended to limit or in any way redefine the invention as claimed in the claims appended hereto.

EXAMPLE 1

Preparation of Pyridine-Soluble Extract from *Corynebacterium Parvum*

*Corynebacterium parvum* (*P.acnes*, Strain 4182) was grown and harvested at 37° C. in NIH thioglycolate broth for between 48 and 72 hours to obtain a whole cell paste. The paste was then washed with 500 ml of distilled water. 90 grams (wet weight) of the washed paste was mixed with 200 ml. of neat pyridine and centrifuged at 1700×g for one hour at 4° C. A pyridine-soluble extract was removed as a supernatant fraction. The remaining residue was extracted with additional pyridine under identical conditions as described above. Following filtration, using Whatman No. 1 paper, the pyridine extracts were pooled and the solvent was removed by evaporation at 50° C. in a Buchi Rotavapor (Brinkmann Instruments, Westbury, N.Y.). The dried pyridine extract was extensively dialyzed against distilled water and then lyophilized. The resulting purified pyridine extract contained about 12% by weight of protein, about 12% by weight of sugar and about 45% by weight of fatty acids. The extract was examined under an electron microscope and found to be free of contaminating whole cells and cell wall fragments. The yield of the pyridine-soluble extract was 9% (8.1 g.).

EXAMPLE 2

Preparation of Pyridine-Soluble Extract from *M.bovis* Strain BCG

*M. bovis* strain BCG was grown and harvested in Sautons medium at 37° C. for between 3-4 weeks to obtain a washed whole cell paste. 50 grams (wet weight) of the washed paste was then treated in the same manner as Example 1 to produce a yield of the pyridine-soluble extract of 7% (3.5 g.). The extract contained 15% by weight of protein, 10% by weight of sugar and 52% by weight of of fatty acids.

EXAMPLE 3

Guinea-Pig Line-10 Tumor Tests

Seven strain 2 guinea pigs having Line-10 tumor growths of about 9 mm in diameter were injected once with 0.4 ml of a sterile oil droplet emulsion, i.e., Drakeol 6 VR mineral oil (Pennsylvania Refining Company, Butler, PA.), containing 300 micrograms of the pyridine-soluble extract prepared in accordance with Example 1 and 50 micrograms of cell wall skeleton, directly into the tumor tissue.

After three months, the animals were examined and in 6 of the 7 animals, total regression had occurred.

In a control experiment, six strain 2 guinea pigs having Line-10 tumor growths of about 9 mm in diameter were injected once with 0.4 ml of the sterile oil droplet emulsion described above without the pyridine extract or cell wall skeleton. The injections were made directly into the tumor tissue. None of the six tumors showed any signs of regression after three months.

What is claimed is:

1. A method of producing a purified pyridine-soluble extract of a microorganism selected from the group consisting of *M. smegmatis, M.phlei, Nocardia rubra, Nocardia asteroides, Corynebacterium diphtheriae, Corynebacterium parvum, M.Kansasii, M. tuberculosis* (strain H 37 RV and Ayoma B), *M. Bovis* Strain BCG, *E. coli, B. abortus* and *Coxielle burnetti*, comprising:
   (a) preparing a whole cell paste of said microorganism;
   (b) washing said paste;
   (c) treating said paste with pyridine to produce an extract and a residue;
   (d) removing said pyridine from said extract; and
   (e) dialyzing said dried extract to obtain purified pyridine-soluble extract.

2. The process of claim 1 further comprising lyophilizing said purified pyridine-soluble extract.

3. The process of claim 1 further comprising treating said residue with pyridine to obtain additional amounts of said pyridine-soluble extract.

4. A pyridine-soluble extract product obtained by the method of claim 1 from a microorganism selected from the group consisting of *M. smegmatis, M.phlei, Nocardia rubra, Nocardia asteroides, Corynebacterium diphtheriae, Corynebacterium parvum, M.Kansasii, M. tuberculosis* (strain H 37 RV and Ayoma B), *M. Bovis* Strain BCG, *E. coli, B. abortus* and *Coxielle burnetti.*

5. A pharmaceutical composition for treating tumors selected from the group consisting of bovine squamous cell carcinoma, bovine fibrosarcoma, equine sarcoid, equine melanoma, equine squamous cell carcinoma, canine mammary tumors, canine adenoma and canine melanoma comprising an anti-tumor effective amount of the product of claim 4 in combination with an anti-tumor effective amount of a cell wall skeleton and a pharmaceutically acceptable carrier.

6. The composition of claim 5 in lyophilized form.

7. The composition of claim 5 wherein said carrier is an oil droplet emulsion.

8. The composition of claim 5 wherein the amount of each of said pyridine-soluble extract product and cell wall skeleton is up to about 40 milligrams.

9. The composition of claim 8 where the amount of said pyridine-soluble extract product is between about 200 and 5,000 micrograms and the amount of cell wall skeleton is between about 50 and 2,000 micrograms.

* * * * *